US010894009B2

(12) United States Patent
Sakiyama et al.

(10) Patent No.: US 10,894,009 B2
(45) Date of Patent: Jan. 19, 2021

(54) TOPICAL AGENT FOR TRANSDERMAL ADMINISTRATION

(71) Applicant: MARUHO CO., LTD., Osaka (JP)

(72) Inventors: Hiroki Sakiyama, Kyoto (JP); Noriaki Kaneda, Kyoto (JP); Tomomi Shigeno, Kyoto (JP)

(73) Assignee: MARUHO CO., LTD., Osaka (JP)

(*) Notice: Subject to any disclaimer, the term of this patent is extended or adjusted under 35 U.S.C. 154(b) by 0 days.

(21) Appl. No.: 15/112,021

(22) PCT Filed: Jan. 14, 2015

(86) PCT No.: PCT/JP2015/050713
§ 371 (c)(1),
(2) Date: Jul. 15, 2016

(87) PCT Pub. No.: WO2015/108045
PCT Pub. Date: Jul. 23, 2015

(65) Prior Publication Data
US 2016/0374920 A1    Dec. 29, 2016

(30) Foreign Application Priority Data
Jan. 16, 2014   (JP) .................................. 2014-006169

(51) Int. Cl.
| *A61K 8/64* | (2006.01) |
| *A61K 9/00* | (2006.01) |
| *A61K 47/08* | (2006.01) |
| *A61K 47/10* | (2017.01) |
| *A61K 47/14* | (2017.01) |
| *A61K 8/34* | (2006.01) |
| *A61K 8/35* | (2006.01) |
| *A61K 8/37* | (2006.01) |
| *A61Q 7/00* | (2006.01) |
| *A61K 38/13* | (2006.01) |

(52) U.S. Cl.
CPC ................. *A61K 8/64* (2013.01); *A61K 8/34* (2013.01); *A61K 8/35* (2013.01); *A61K 8/37* (2013.01); *A61K 9/0014* (2013.01); *A61K 47/08* (2013.01); *A61K 47/10* (2013.01); *A61K 47/14* (2013.01); *A61Q 7/00* (2013.01); *A61K 38/13* (2013.01)

(58) Field of Classification Search
CPC ........ A61K 38/13; A61K 47/08; A61K 47/10; A61K 47/14; A61K 8/34; A61K 8/35; A61K 8/37; A61K 8/64; A61K 9/0014; A61Q 7/00
See application file for complete search history.

(56) References Cited

U.S. PATENT DOCUMENTS

| 8,663,692 B1 * | 3/2014 | Muller ................. A61K 9/0014 424/401 |
| 2005/0074468 A1 * | 4/2005 | Kim ...................... A61K 8/025 424/400 |
| 2013/0184243 A1 * | 7/2013 | Alonso ................ A61K 31/131 514/171 |

FOREIGN PATENT DOCUMENTS

| EP | 0547229 A1 | 6/1993 | |
| GB | 2228198 A | 8/1990 | |
| JP | S62-019513 A | 1/1987 | |
| JP | H02-255623 A | 10/1990 | |
| JP | H07-188046 A | 7/1995 | |
| JP | H07-316023 A | 12/1995 | |
| WO | WO-9211860 A1 * | 7/1992 | ........... A61K 9/0014 |
| WO | WO 1993/000106 A1 | 1/1993 | |
| WO | WO-9840051 A1 * | 9/1998 | ........... A61K 9/1075 |
| WO | WO-2012107573 A1 * | 8/2012 | ........... A61K 9/0014 |

OTHER PUBLICATIONS

Anonymous. MIGLYOL 812. www.petercremerna.com/products/159339301. (Year: 2014).*
Yokota et al. "Effects of Oral versus Transdermal Administration of Cyclosporine on Phorbol Ester Promotion of Murine Epidermal Carcinogenesis" Cancer Research 49:4586-4590. (Year: 1981).*
Yamamoto and Kato. "Hair growth-stimulating effects of cyclosporin A and FK506, potent immunosuppressants" J. Dermatol. Sci. 7: S47-S54. Abstract only. (Year: 1994).*
Verma and Fahr "Synergistic penetration enhancement effect of ethanol and phospholipids on the topical delivery of cyclosporin A" J. Controlled Release 97:55-66. (Year: 2004).*
Morimoto et al. "Basic Studies on Controlled Transdermal Delivery of Nicardipine Hydrochloride Using Ethylene-Vinyl Acetate and Etheylene-Vinyl Alcohol Copolymer Membranes" Chem. Pharm. Bull. 36:2633-2641. (Year: 1988).*
Lachenmeier D "Safety evaluation of topical applications of ethanol on the skin and inside the oral cavity" J. Occup. Med. Toxicol. 3: 26 (Year: 2008).*
Paudel et al. "Challenges and opportunities in dermal/transdermal delivery" Ther. Deliv. 1:109-131. (Year: 2010).*
Andrysek T "Excipients and their role in absorption: influencing bioavailability of cyclosporine by triglycerides and polyglycerol esters" Biomed Pap Med Fac Univ Palacky Olomouc Czech Repub 150:227-233. (Year: 2006).*
De Prost et al., "Placebo-Controlled Trial of Topical Cyclosporin in Severe Alopecia Areata," *The Lancet*, 2(8510): 803-804 (Oct. 4, 1986).

(Continued)

*Primary Examiner* — Larry D Riggs, II
*Assistant Examiner* — Zachary J Miknis
(74) *Attorney, Agent, or Firm* — Leydig, Voit & Mayer, Ltd.

(57) ABSTRACT

The present invention aims to provide a cyclosporine external preparation showing improved transdermal absorbability of cyclosporine. The present invention provides an external preparation containing cyclosporine and a ketone.

16 Claims, 3 Drawing Sheets

(56) References Cited

OTHER PUBLICATIONS

De Prost et al., "Treatment of Severe Alopecia Areata by Topical Applications of Cyclosporine: Comparative Trial Versus Placebo in 43 Patients," *Transplantation Proceedings*, 20(3—Suppl. 4): 112-113 (Jun. 1988).

Liu et al., "Effect of vehicles and enhancers on the topical delivery of cyclosporin A," *International Journal of Pharmaceutics*, 311: 182-186 (2006).

Pigatto et al., "Low Concentration of Topical Cyclosporin A for Severe Alopecia Areata," *Ann. Ital. Dermatol. Clin. Sper*, 42: 377-382 (1988).

Japanese Patent Office, International Search Report in International Patent Application No. PCT/JP2015/050713 (Feb. 17, 2015).

Yokota et al., "Effects of Oral versus Topical Administration of Cyclosporine on Phorbol Ester Promotion of Murine Epidermal Carcinogenesis," *Cancer Res.*, 49(16): 4586-4590 (1989).

European Patent Office, Extended European Search Report in European Patent Application No. 15737583.3 (Aug. 9, 2017).

Sugibayashi (Editor), Skin Permeation and Disposition of Therapeutic and Cosmeceutical Compounds (Springer Japan KK, 2017), sections 2.3-2.5 at pp. 16-21 (2017).

\* cited by examiner

TOPICAL AGENT FOR TRANSDERMAL ADMINISTRATION

CROSS-REFERENCE TO RELATED APPLICATIONS

This patent application is the U.S. national phase of International Patent Application No. PCT/JP2015/050713, filed on Jan. 14, 2015, which claims the benefit of Japanese Patent Application No. 2014-006169, filed Jan. 16, 2014, the disclosures of which are incorporated herein by reference in their entireties for all purposes.

TECHNICAL FIELD

The present invention relates to a cyclosporine external preparation showing improved transdermal absorbability of cyclosporine.

BACKGROUND ART

Cyclosporine is a compound having an immunosuppressive action and a hair restoration action, and is known to be effective for dermatic diseases such as psoriasis, atopic dermatitis, alopecia areata and the like. However, since it has a large molecular weight of about 1200, transdermal absorption thereof is difficult. Transdermal absorption from human skin is more difficult since the stratum corneum layer thereof is thicker than that of animals.

Non-patent document 1 describes that a plurality of vehicles for the topical delivery of cyclosporine were studied and 40% ethanol showed the highest efficiency.

Non-patent document 2 describes a treatment effect provided by transdermal administration of a 0.2% solution of cyclosporine dissolved in castor oil on alopecia areata. However, in a castor oil preparation, cyclosporine cannot be dissolved at a high concentration, a texture during use is poor and a problem of skin irritation occurs.

Patent document 1 describes cyclosporine A as other compound having a hair restoration effect, which can be used in combination in a hair restoration agent containing an arginine-analogous nitric oxide synthase inhibitor. Moreover, non-patent documents 3 and 4 study a alopecia areata treatment effect by topical application of cyclosporine A.

DOCUMENT LIST

Patent Document

Patent document 1: JP-A-7-316023

Non-Patent Documents

Non-patent document 1: International Journal of pharmaceutics 311 (2006) 182-186
Non-patent document 2: Ann ital dermatol clin sper 42 (1988) 377-382
Non-patent document 3: Lancet 1986 ii 803-804
Non-patent document 4: Transplantation Proceedings Vol XX No 3 Suppl 4 (June) 1988 p. 112-113

SUMMARY OF THE INVENTION

Problems to be Solved by the Invention

Pathology of alopecia areata is occurrence of circular to patchy hair loss spots in any site where the hair exists. Histopathologically, it is characterized by perifollicular lymphocyte infiltration, and this disease is known to be an autoimmune disease, which is based on abnormality in local immunity. In view of such pathology and etiology, cyclosporine A (CyA) has been additionally used for the treatment of alopecia areata (non-approved indication). A commercially available oral preparation or injection thereof is used for the treatment; however, calcineurin inhibitors including CyA have difficulty caused by side effects. It is known that systemic administration thereof cause hypertension, kidney dysfunction and other various side effects. In addition, there is a risk of drug interaction with other agents, and use thereof is restricted in some occasions.

Therefore, it is considered that the systemic side effects can be reduced, the concentration of the active ingredient can be increased at the disease site, and topical effectiveness can be achieved by forming CyA for external use and applying same in topical treatments.

As mentioned above, however, cyclosporine is difficult for transdermal absorption, and a cyclosporine external preparation enabling sufficient transdermal absorption through human skin as well is not known.

The present invention aims to provide a cyclosporine external preparation showing improved transdermal absorbability of cyclosporine.

Means of Solving the Problems

The present inventors have conducted intensive studies in an attempt to solve the aforementioned problems and found that the transdermal absorbability of cyclosporine can be improved by adding a ketone such as methyl ethyl ketone and the like. The present inventors conducted further studies based on such findings and completed the present invention.

Therefore, the present invention provides the following.

[1] An external preparation comprising cyclosporine and a ketone.

[2] The external preparation of the above-mentioned [1], wherein the ketone is selected from the group consisting of methyl ethyl ketone, acetone and methyl isobutyl ketone.

[3] The external preparation of the above-mentioned [1] or [2], further comprising ethanol.

[4] The external preparation of any of the above-mentioned [1]-[3], further comprising a fatty acid ester.

[5] The external preparation of the above-mentioned [4], wherein the fatty acid ester is selected from the group consisting of fatty acid monoester and medium-chain triglyceride.

[6] The external preparation of the above-mentioned [4], wherein the fatty acid ester is selected from the group consisting of isopropyl myristate, isopropyl palmitate and caprylic/capric triglyceride.

[7] The external preparation of the above-mentioned [4], wherein the fatty acid ester is isopropyl myristate and caprylic/capric triglyceride.

[8] The external preparation of any of the above-mentioned [1]-[7], wherein the external preparation is liquid.

[9] The external preparation of any of the above-mentioned [1]-[8], which is substantially free of water as a dissolving agent.

[10] The external preparation of any of the above-mentioned [1]-[9], which is a hair growth inducer.

Effect of the Invention

The external preparation of the present invention is superior in transdermal absorbability of cyclosporine, and particularly enables sufficient transdermal absorption through human skin as well.

Since the external preparation of the present invention can promote transdermal absorption of cyclosporine to ensure delivery to the lower layer of skin, it can treat alopecia such as alopecia areata and the like, psoriasis, atopic dermatitis and the like.

The external preparation of the present invention can reduce systemic side effects such as hypertension, kidney dysfunction and the like due to the oral administration of cyclosporine, and can exhibit topical effectiveness.

The external preparation of the present invention is superior in transdermal absorbability, and can be efficiently administered topically. Therefore, the effects of cyclosporine such as induction of hair growth and the like can be effectively exhibited, and low dosing is possible.

The external preparation of the present invention is superior in preservation stability (stability of active ingredient, preparation stability), and causes less skin irritation.

DESCRIPTION OF EMBODIMENTS

Figure 1:
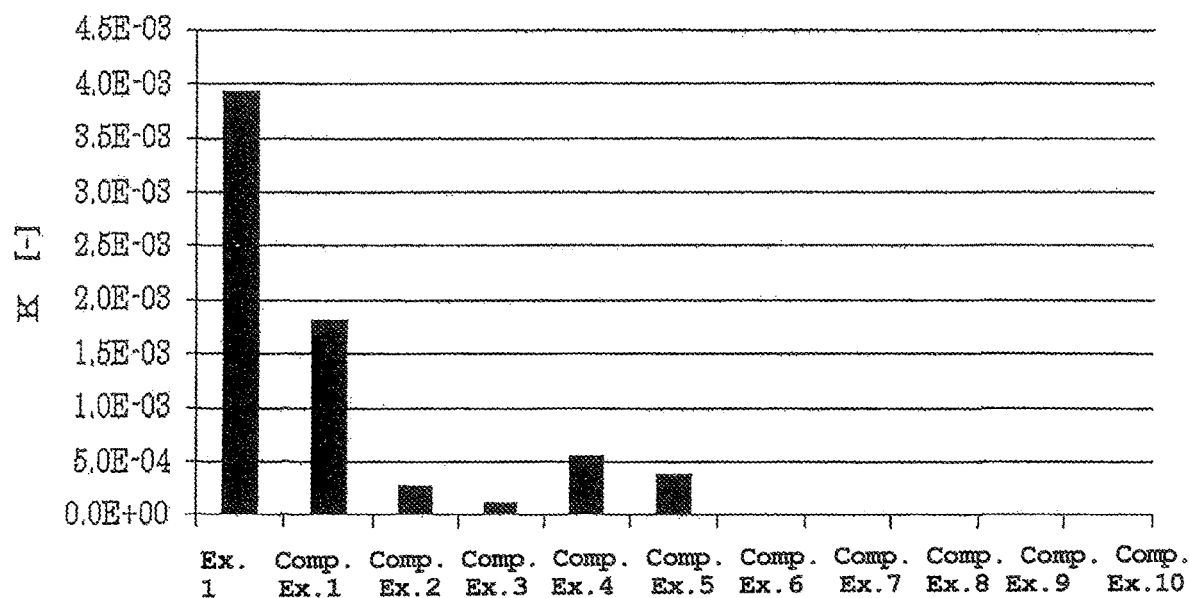
FIG. 1 shows the results of Experimental Example 1.

The external preparation of the present invention contains cyclosporine as a drug.

In the present specification, cyclosporine is a concept encompassing cyclosporine A, cyclosporine B, cyclosporine C, cyclosporine D, cyclosporine H and the like. In the present invention, cyclosporine is preferably cyclosporine A.

The content percentage of cyclosporine in the external preparation of the present invention is generally not less than 1 wt %, preferably not less than 1.25 wt %, further preferably not less than 2 wt %, more preferably not less than 2.5 wt %, particularly preferably not less than 5 wt %, relative to the total amount of the preparation. The content percentage of cyclosporine in the total amount of the preparation is generally not more than 50 wt %, preferably not more than 30 wt %, further preferably not more than 10 wt %.

The content percentage of cyclosporine in the external preparation of the present invention is generally 1-50 wt %, preferably 2.5-30 wt %, further preferably 5-30 wt %, relative to the total amount of the preparation. The content percentage of cyclosporine in one embodiment is 1.25-10 wt %, 2-10 wt %, relative to the total amount of the preparation.

The external preparation of the present invention contains a ketone. In the present invention, examples of the ketone include a compound R(R')C=O wherein R and R' are each an alkyl having 1-4 carbon atoms, specifically, for example, methyl ethyl ketone, acetone, methyl isobutyl ketone and the like, and methyl ethyl ketone is preferable.

The content percentage of ketone in the external preparation of the present invention is generally 1-99 wt %, preferably 5-90 wt %, more preferably 10-50 wt %, further preferably 10-30 wt %, relative to the total amount of the preparation. When ketone is less than 1 wt %, the transdermal absorbability tends to decrease. To reduce the local irritation, the content of ketone is preferably not more than 50 wt %.

The external preparation of the present invention preferably contains ethanol.

In the present invention, ethanol is preferably anhydrous ethanol. Examples of the anhydrous ethanol include anhydrous ethanol defined in the Japanese Pharmacopoeia 16th Edition.

The content percentage of ethanol in the external preparation of the present invention is generally 3-90 wt %, preferably 5-70 wt %, more preferably 8-50 wt %, further preferably 15-40 wt %, relative to the total amount of the preparation. When ethanol is less than 3 wt %, the transdermal absorbability tends to decrease. To reduce the local irritation, the content of ethanol is preferably not more than 50 wt %.

The external preparation of the present invention preferably contains fatty acid ester. Fatty acid ester is used as a non-volatile base.

In the present invention, examples of the fatty acid ester include esters of aliphatic monocarboxylic acid, aliphatic dicarboxylic acid and the like and alcohol.

Examples of the fatty acid ester include fatty acid monoesters (e.g., ester of monovalent alcohol having 1-22 (preferably 1-16, more preferably 1-3) carbon atoms (e.g., methyl alcohol, ethyl alcohol, propyl alcohol, isopropyl alcohol, lauryl alcohol, myristyl alcohol, palmityl alcohol, stearyl alcohol, isostearyl alcohol, cetostearyl alcohol, 2-hexadecyl alcohol, octyldodecyl alcohol, behenyl alcohol) and monocarboxylic acid having 6-22 (preferably 14-16) carbon atoms (e.g., caproic acid, caprylic acid, capric acid, lauric acid, myristic acid, palmitic acid, stearic acid, behenic acid, isostearic acid) (e.g., isopropyl myristate, isopropyl palmitate, 2-hexadecyl isostearate)); fatty acid diester (e.g., ester of divalent alcohol having 2-22 carbon atoms (e.g., ethylene glycol, propylene glycol, butyleneglycol, hexanediol, octanediol, docosanediol) and fatty acid having 6-22 carbon atoms (e.g., caproic acid, caprylic acid, capric acid, lauric acid, myristic acid, palmitic acid, stearic acid, behenic acid, isostearic acid), or ester of dicarboxylic acid having 6-10 carbon atoms (e.g., adipic acid, sebacic acid) and alcohol having 1-22 (preferably 1-3) carbon atoms (e.g., methyl alcohol, ethyl alcohol, propyl alcohol, isopropyl alcohol, lauryl alcohol, myristyl alcohol, palmityl alcohol, stearyl alcohol, isostearyl alcohol, cetostearyl alcohol, 2-hexadecyl alcohol, octyldodecyl alcohol, behenyl alcohol) (e.g., diisopropyl adipate, diethyl sebacate, diisopropyl sebacicate)); and glycerin fatty acid ester (e.g., ester of glycerin and fatty acid having 4-22 carbon atoms (e.g., butyric acid, caproic acid, caprylic acid, capric acid, lauric acid, myristic acid, palmitic acid, stearic acid, behenic acid, isostearic acid)).

The glycerin fatty acid ester is preferably middle chain fatty acid glyceride, more preferably medium-chain triglyceride; the medium-chain triglyceride is triglyceride with fatty acid having 4-18 (preferably 8-10) carbon atoms (e.g., succinic acid, caproic acid, caprylic acid, capric acid, lauric acid, linoleic acid), and caprylic/capric triglyceride can be specifically mentioned. As the medium-chain triglyceride, miglyol 810 (caprylic/capric triglyceride, Mitsuba Trading Co., Ltd.) can be preferably used.

One or more kinds of fatty acid ester can be used in combination.

In the present invention, fatty acid ester is preferably fatty acid monoester (particularly, isopropyl myristate, isopropyl palmitate), diethyl sebacate, glycerin fatty acid ester (preferably, medium-chain triglyceride (particularly, caprylic/capric triglyceride)), more preferably isopropyl myristate or isopropyl palmitate.

The content percentage of fatty acid ester in the external preparation of the present invention is generally 1-98 wt %, preferably 3-50 wt %, more preferably 5-35 wt %, further preferably 5-30 wt %, relative to the total amount of the preparation.

When fatty acid ester is less than 1 wt %, cyclosporine tends to be precipitated when applied to the affected part, as a result of volatilization of ketone, lower alcohols (e.g., ethanol) and the like used as dissolving agents. To reduce the local irritation, it is preferably not more than 50 wt %.

When fatty acid monoester (particularly isopropyl myristate) and glycerin fatty acid ester (preferably medium-chain triglyceride (particularly caprylic/capric triglyceride)) are used in combination in the external preparation of the present invention, the content percentage of fatty acid monoester (particularly isopropyl myristate) is generally 2-90 wt %, preferably 3-50 wt %, further preferably 5-30 wt %, relative to the total amount of the preparation, and the content percentage of glycerin fatty acid ester (preferably medium-chain triglyceride (particularly caprylic/capric triglyceride)) is generally 2-90 wt %, preferably 3-50 wt %, further preferably 5-30 wt %, relative to the total amount of the preparation.

The external preparation of the present invention is characterized by the use of the aforementioned ketone (preferably, ketone and ethanol and/or fatty acid ester) as a dissolving agent for dissolving cyclosporine. Since cyclosporine is finely dissolved in the dissolving agent in the external preparation of the present invention, superior transdermal absorbability can be exhibited.

The external preparation of the present invention optionally contains a dissolving agent other than those mentioned above (e.g., water, polyethylene glycol (e.g., macrogol 400), triacetine, oleyl alcohol, 2-ethyl-1,3-hexanediol, propylene glycol, dipropylene glycol, 1,3-butylene glycol, glycerin, isopropanol, light liquid paraffin, squalane, dimethylpolysiloxane, ethylene glycol salicylate etc.) as long as the effect of the present invention is not inhibited. In the external preparation of the present invention, the content of the dissolving agent other than ketone, ethanol and fatty acid ester is preferably not more than 40 wt %, more preferably not more than 20 wt %, further preferably not more than 10 wt %, of the whole dissolving agent. In the present specification, the total weight of the dissolving agent does not include the weight of a component (e.g., 1-menthol etc.) that does not act as a dissolving agent.

In the external preparation of the present invention, the content percentage of water relative to the whole dissolving agent is generally not more than 40 wt % or not more than 35 wt %, since the solubility of cyclosporine in the dissolving agent and transdermal absorbability decrease, and the dissolving agent is more preferably substantially free of water. In the present specification, the "dissolving agent being substantially free of water" means that the content percentage of water in the whole dissolving agent that dissolves cyclosporine is generally not more than 10 wt %, preferably not more than 5 wt %, more preferably not more than 3 wt %, further preferably nil. It is only necessary that the dissolving agent and water not be blended, and a dissolving agent that has dissolved cyclosporine, such as ketone and the like, may be emulsified with water by the use of a surfactant to give cream or emulsion lotion.

Examples of the dosage form of the external preparation of the present invention include liquid, cream, lotion and gel, with preference given to liquid.

The external preparation of the present invention optionally contains, besides the above-mentioned components, additives generally used in the field of external preparation, for example, surfactant, thickener, stabilizer, preservative, pH adjuster and flavor.

The external preparation of the present invention can be produced by a method known in the field of external preparations. For example, a liquid can be produced by dissolving cyclosporine in a mixed solution of methyl ethyl ketone and an additive to be optionally added (anhydrous ethanol, isopropyl myristate, medium-chain triglyceride, 1-menthol etc.).

As the external preparation of the present invention, a liquid containing cyclosporine (preferably cyclosporine A) 2.5-30 wt %, methyl ethyl ketone 10-30 wt %, ethanol (preferably anhydrous ethanol) 10-30 wt %, isopropyl myristate 5-30 wt %, and medium-chain triglyceride (preferably caprylic/capric triglyceride) 5-30 wt % is preferable.

In addition, a liquid containing cyclosporine (preferably cyclosporine A) 2.5-30 wt %, methyl ethyl ketone 10-30 wt %, ethanol (preferably anhydrous ethanol) 10-30 wt %, isopropyl myristate 5-30 wt %, medium-chain triglyceride (preferably caprylic/capric triglyceride) 5-30 wt %, and a flavor (e.g., 1-menthol) 0.5-5 wt % is preferable.

The external preparation of the present invention can be used safely for human, mammals (e.g., rodents such as mouse, hamster, guinea pig, rat, rabbit and the like, dog, cat, goat, sheep, bovine, swine, monkey etc.).

The external preparation of the present invention is useful for the treatment of, for example, alopecia such as alopecia areata (e.g., alopecia universalis, single alopecia, multiple alopecia) and the like, psoriasis, atopic dermatitis, contact dermatitis, seborrheic dermatitis, prurigo and the like. Among others, the external preparation of the present invention is useful as a hair growth inducer (particularly a hair growth inducer for alopecia areata).

Alopecia areata is triggered by autoimmunity. Therefore, a cyclosporine external preparation concurrently having such immunosuppressive action and a hair restoration action is considered to provide a therapeutic drug effective for alopecia areata. In fact, the aforementioned non-patent documents 2-4 and patent document 1 show a hair growth effect by transdermal administration of cyclosporine.

While the dose of the external preparation of the present invention varies depending on the target disease, severity of the disease and the like, when it is used as a hair growth inducer, the dose is, for example, 0.1 $\mu g/cm^2$-200 $\mu g/cm^2$ as cyclosporine per single administration, which can be applied to the lesion twice per day.

EXAMPLES

The present invention is explained in more detail in the following by referring to Examples, Comparative Examples and Experimental Examples, which are not to be construed as limitative.

In the Examples and Comparative Examples, miglyol 810 (caprylic/capric triglyceride, Mitsuba Trading Co., Ltd.) was used as medium-chain triglyceride; and the Japanese Pharmacopoeia anhydrous ethanol (Amakasu Chemical Industries) was used as anhydrous ethanol.

Experimental Example 1

In Vitro Hairless Mouse Skin Permeability Test

The liquid of Example 1 obtained by dissolving cyclosporine A in methyl ethyl ketone, and the liquids of Comparative Examples 1-10 obtained by dissolving cyclosporine A in a dissolving agent actually used as the pharmaceutical additive described in Table 1 were subjected to an in vitro skin permeability test by using a Franz vertical diffusion cell (vertical Franz cell, receptor volume: 7 mL, effective diffusion area: 1.77 cm$^2$). The concentration of cyclosporine A in each liquid was 10% of the saturation concentration of cyclosporine A in each dissolving agent (Table 1).

As a permeation membrane, the skin of hairless mouse (Laboskin, Hos-HR1, male, 7-week-old, Hoshino Laboratory Animals, Inc.) was used, and PBS containing 1% bovine serum albumin (Dulbecco PBS (−), NISSUI PHARMACEUTICAL CO., LTD.; bovine serum albumin, Nacalai Tesque) was used as a receptor solution. Each liquid (1000 μL) was applied onto a permeation membrane, the receptor solution was stirred while maintaining at 32° C., and the receptor solution (500 μL) was collected over time as an analysis sample.

The concentration of cyclosporine A in the receptor solution was quantified by a liquid chromatography-tandem mass spectrometry apparatus (LC/MS/MS). Based on the results thereof, the coefficient of partition K between preparation-skin was calculated as an index of cyclosporine A concentration in the skin. The calculating formula of the coefficient of partition K is as shown below. The results are shown in FIG. 1 (mean, n=3).

TABLE 1

| | dissolving agent | cyclosporine A concentration (w/v %) |
|---|---|---|
| Ex. 1 | methyl ethyl ketone | 6.216 |
| Comp. Ex. 1 | anhydrous ethanol | 5.79 |
| Comp. Ex. 2 | isopropyl myristate | 0.428 |
| Comp. Ex. 3 | macrogol 400 | 1.956 |
| Comp. Ex. 4 | medium-chain triglyceride | 1.496 |
| Comp. Ex. 5 | diethyl sebacate | 2.272 |
| Comp. Ex. 6 | triacetine | 2.3 |
| Comp. Ex. 7 | oleyl alcohol | 2.026 |
| Comp. Ex. 8 | 2-ethyl-1,3-hexanediol | 2.838 |
| Comp. Ex. 9 | propylene glycol | 4.194 |
| Comp. Ex. 10 | dipropyleneglycol | 4.064 |

$$K(-) = \frac{6 \times \text{permeation rate (ng/cm}^2\text{/hr)} \times \text{lag time (hr)}}{\text{skin thickness (cm)} \times \text{concentration of cyclosporine } A \text{ in preparation (ng/cm}^2\text{)}}$$

Experimental Example 2

In Vitro Hairless Mouse Skin Permeability Test

Figure 2:
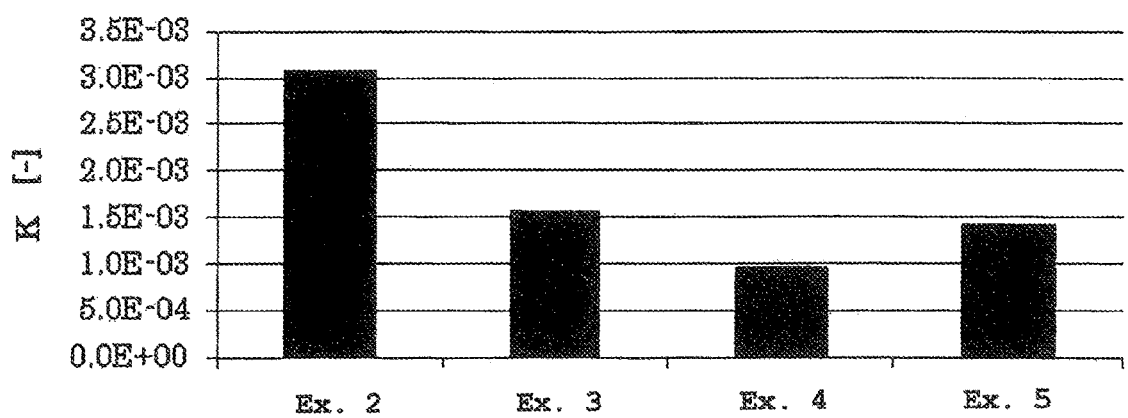
FIG. 2 shows the results of Experimental Example 2.

The liquids of Examples 2-5 obtained by dissolving cyclosporine A in a 50:50 (weight ratio) mixed solution of methyl ethyl ketone, and anhydrous ethanol, isopropyl myristate, medium-chain triglyceride or diethyl sebacate were subjected to a skin permeability test by a method similar to that in Experimental Example 1, and the coefficient of partition K was calculated. The concentration of cyclosporine A in the liquids was 6.216 (w/v %) (10% of saturation concentration of cyclosporine A in methyl ethyl ketone) (Table 2). The results are shown in FIG. 2.

TABLE 2

| | dissolving agent | cyclosporine A concentration (w/v %) |
|---|---|---|
| Ex. 2 | methyl ethyl ketone + anhydrous ethanol | 6.216 |
| Ex. 3 | methyl ethyl ketone + isopropyl myristate | 6.216 |
| Ex. 4 | methyl ethyl ketone + medium-chain triglyceride | 6.216 |
| Ex. 5 | methyl ethyl ketone + diethyl sebacate | 6.216 |

Experimental Example 3

In Vitro Hairless Mouse Skin Permeability Test

The liquids of Examples 6, 7, and Comparative Examples 11, 12 obtained by mixing the components shown in Table 3 were applied to the skin by a method similar to that in Experimental Example 1 except that the applied dose of each liquid was set to 500 μL. At 24 hr from liquid application, the skin was wiped clean, and the dermis was collected by heat separation (60° C., 1 min, dry incubation).

Figure 3:
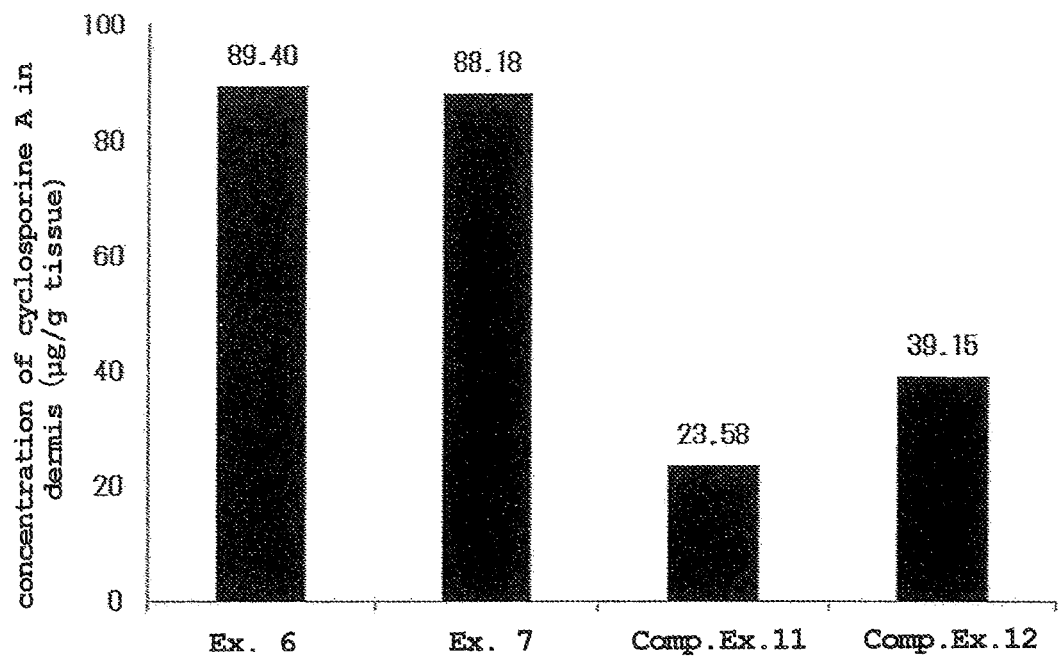
FIG. 3 shows the results of Experimental Example 3.

The concentration of cyclosporine A in the dermis was quantified by a liquid chromatography-tandem mass spectrometry apparatus (LC/MS/MS). The results are shown in FIG. 3 (mean, n=3).

TABLE 3

| | formulation amount (wt %) | | | |
|---|---|---|---|---|
| component | Ex. 6 | Ex. 7 | Comp. Ex. 11 | Comp. Ex. 12 |
| cyclosporine A | 2.5 | 2.5 | 2.5 | 2.5 |
| methyl ethyl ketone | 97.5 | 48.75 | — | — |
| anhydrous ethanol | — | — | 39.0 | 97.5 |
| purified water | — | — | 58.5 | — |
| isopropyl myristate | — | 48.75 | — | — |

Since cyclosporine exhibits an effect in the skin, the concentration in the skin was used as an index of transdermal absorbability. While the aforementioned non-patent document 1 describes that the ethanol/water system is superior in transdermal absorbability, as is clear from the results of Example 6 and Comparative Example 11, the liquid of the present invention using methyl ethyl ketone showed remarkably-improved transdermal absorbability as compared to the dissolving agent of the document. In addition, it is considered that organic solvent-water will not show good transdermal absorbability in actual clinical use, since it has high volatility.

Experimental Example 4

In Vitro Hairless Mouse Skin Permeability Test

Figure 4:
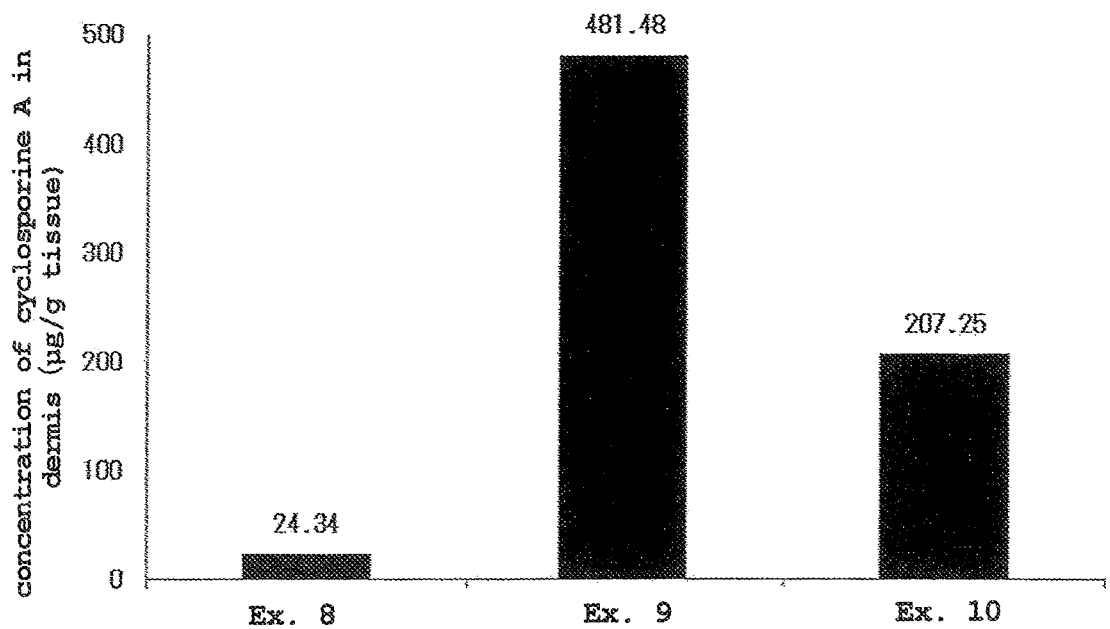
FIG. 4 shows the results of Experimental Example 4.

The liquids of Examples 8-10 obtained by mixing the components shown in Table 4 were subjected to a skin permeability test by a method similar to that in Experimental Example 3 except that the applied dose of each liquid was set to 10 µL, and the concentration of cyclosporine A in the dermis was quantified. The results are shown in FIG. 4 (mean, n=3).

Example 9 using a combination of methyl ethyl ketone, anhydrous ethanol and isopropyl myristate as a dissolving agent showed a particularly high concentration in the skin, thus showing particularly high transdermal absorbability.

TABLE 4

| component | formulation amount (wt %) | | |
|---|---|---|---|
| | Ex. 8 | Ex. 9 | Ex. 10 |
| cyclosporine A | 10 | 10 | 10 |
| methyl ethyl ketone | 30 | 30 | 30 |
| anhydrous ethanol | 30 | 30 | — |
| purified water | 30 | — | — |
| isopropyl myristate | — | 30 | 30 |
| light liquid paraffin | — | — | 30 |

Experimental Example 5

In Vitro Human Skin Permeability Test

The liquid of Comparative Example 13 (0.2 wt % solution of cyclosporine dissolved in castor oil described in the aforementioned non-patent document 2), the liquid of Example 9, and the liquids of Examples 11-14 obtained by mixing the components shown in Table 5 were subjected to a skin permeability test by a method similar to that in Experimental Example 3 except that the skin from a human dead body (male, white, back skin, Human and Animal Bridging Research Organization) was used as the permeation membrane and the is applied dose of each liquid was set to 10 µL, and the concentration of cyclosporine A in the dermis was quantified.

Figure 5:
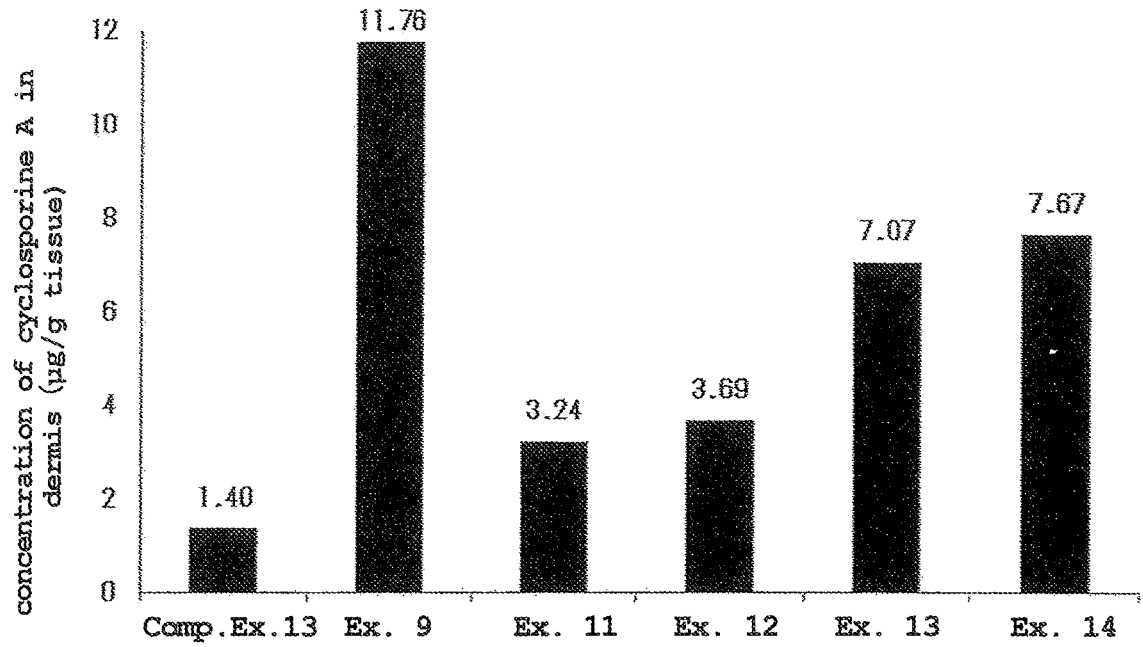
FIG. 5 shows the results of Experimental Example 5.

The results are shown in FIG. 5 (mean, n=3). The Example liquids showed transdermal absorbability exceeding that of Comparative Example 13 acknowledged to be effective for alopecia areata.

TABLE 5

| component | formulation amount (wt %) | | | | | |
|---|---|---|---|---|---|---|
| | Comp. Ex. 13 | Ex. 9 | Ex. 11 | Ex. 12 | Ex. 13 | Ex. 14 |
| cyclosporine A | 0.2 | 10 | 10 | 10 | 10 | 10 |
| methyl ethyl ketone | — | 30 | 30 | 10 | 30 | 30 |
| anhydrous ethanol | — | 30 | 30 | 50 | 28 | 8 |
| castor oil | 99.8 | — | — | — | — | — |
| isopropyl myristate | — | 30 | 5 | 5 | 5 | — |
| medium-chain triglyceride | — | — | 25 | 25 | 25 | 25 |
| l-menthol | — | — | — | — | 2 | 2 |
| isopropyl palmitate | — | — | — | — | — | 10 |
| hexadecyl isostearate | — | — | — | — | — | 15 |

Experimental Example 6

In Vitro Human Skin Permeability Test

Figure 6:
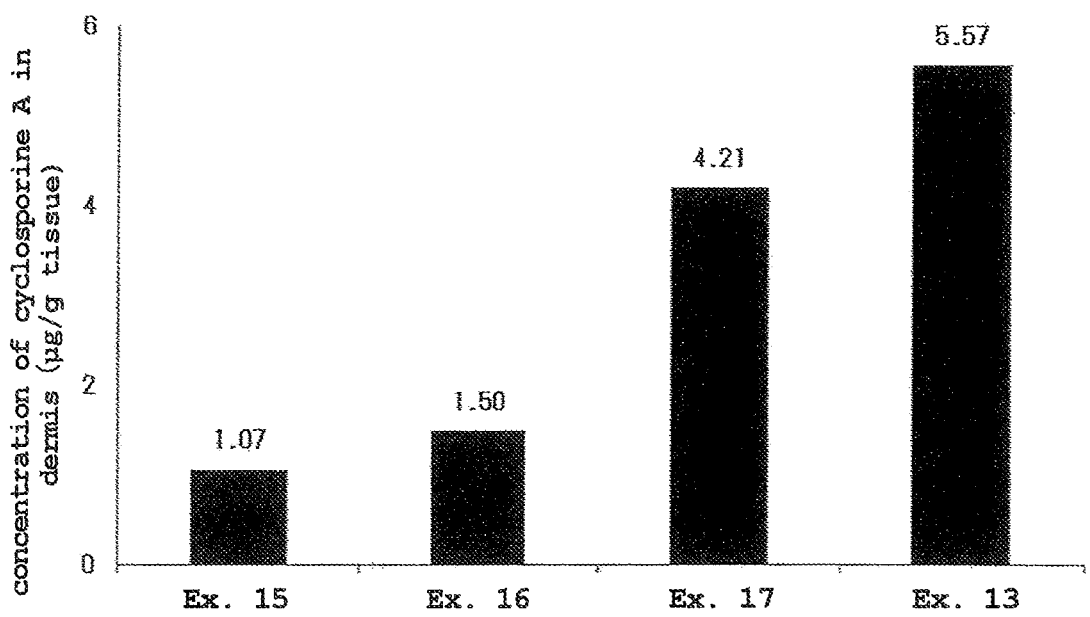
FIG. 6 shows the results of Experimental Example 6.

The liquids of Examples 13, 15-17 obtained by mixing the components shown in Table 6 were subjected to a skin permeability test by a method similar to that in Experimental Example 5, and the concentration of cyclosporine A in the dermis was quantified. The results are shown in FIG. 6 (mean, n=6).

TABLE 6

| component | formulation amount (wt %) | | | |
|---|---|---|---|---|
| | Ex. 15 | Ex. 16 | Ex. 17 | Ex. 13 |
| cyclosporine A | 1.25 | 2.5 | 5 | 10 |
| methyl ethyl ketone | 30 | 30 | 30 | 30 |
| anhydrous ethanol | 36.75 | 35.5 | 33 | 28 |
| isopropyl myristate | 5 | 5 | 5 | 5 |
| medium-chain triglyceride | 25 | 25 | 25 | 25 |
| 1-menthol | 2 | 2 | 2 | 2 |

While the aforementioned non-patent document 1 describes that the ethanol/water system is superior in transdermal absorbability, as is clear from the results of Example 6 and Comparative Example 11 in Experimental Example 3, the liquid of the present invention using methyl ethyl ketone showed remarkably-improved transdermal absorbability as compared to the dissolving agent of the document, and the results of Experimental Example 5 reveal that the liquid of the present invention using methyl ethyl ketone showed transdermal absorbability exceeding that of the 0.2 wt % solution of cyclosporine dissolved in castor oil, which is reported to show a treatment effect on alopecia areata in the aforementioned non-patent document 2. In addition, it is considered that organic solvent-water will not show good transdermal absorbability in actual clinical use, since it has high volatility.

Experimental Example 7

Stability Test

The liquid of Example 13 was evaluated for preparation stability from the active ingredient residual ratio (cyclosporine A residual ratio), property and precipitate of the preparation. The active ingredient residual ratio was quantified by high performance liquid chromatography of the unchanged form in the sample.

As for the active ingredient residual ratio, the samples were preserved at 40° C. or 60° C., for 4 weeks, 8 weeks and 13 weeks and quantified. As a result, the active ingredient residual ratio did not decrease. As for the preparation stability, the samples were preserved at 40° C. for the property, and 5° C. or −5° C. for the precipitate, and the samples at 3 weeks, 8 weeks and 13 weeks after preservation were confirmed by visual observation and microscope. As a result, property change and precipitate were not found.

From the above, it was shown that the liquid of Example 13 is free of a problem in the stability of the active ingredient and preparation stability.

Experimental Example 8

Skin Irritation Test

The liquids of Examples 11, 13 and 14 were evaluated for the cumulative skin irritation by using rabbits. As a result, they were categorized into weak irritants, thus showing no problem in skin irritation. In an ocular irritation study using rabbit, these liquids were categorized into weak irritants, thus also showing no problem in ocular irritation.

INDUSTRIAL APPLICABILITY

According to the present invention, a cyclosporine external preparation showing improved transdermal absorbability of cyclosporine can be provided.

This application is based on a patent application No. 2014-006169 filed in Japan, the contents of which are incorporated in full herein.

The invention claimed is:

1. An external preparation comprising (i) cyclosporine, (ii) methyl ethyl ketone, (iii) ethanol, and (iv) isopropyl myristate,
   wherein
   the cyclosporine is selected from the group consisting of cyclosporine A, cyclosporine B, cyclosporine C, cyclosporine D, and cyclosporine H, and
   the external preparation is a transdermal formulation.

2. The external preparation according to claim 1, which is liquid.

3. The external preparation according to claim 2, wherein the ethanol is anhydrous ethanol.

4. The external preparation according to claim 3, wherein the cyclosporine is cyclosporine A.

5. The external preparation according to claim 2, wherein the cyclosporine is cyclosporine A.

6. The external preparation according to claim 1, which is substantially free of water as a dissolving agent.

7. The external preparation according to claim 6, wherein the ethanol is anhydrous ethanol.

8. The external preparation according to claim 7, wherein the cyclosporine is cyclosporine A.

9. The external preparation according to claim 6, wherein the cyclosporine is cyclosporine A.

10. The external preparation according to claim 1, which is a hair growth inducer.

11. The external preparation according to claim 10, wherein the ethanol is anhydrous ethanol.

12. The external preparation according to claim 11, wherein the cyclosporine is cyclosporine A.

13. The external preparation according to claim 10, wherein the cyclosporine is cyclosporine A.

14. The external preparation according to claim 1, wherein the ethanol is anhydrous ethanol.

15. The external preparation according to claim 14, wherein the cyclosporine is cyclosporine A.

16. The external preparation according to claim 1, wherein the cyclosporine is cyclosporine A.

* * * * *